United States Patent [19]

Ahmed

[11] Patent Number: 4,832,876

[45] Date of Patent: May 23, 1989

[54] PROCESS FOR THE MANUFACTURE OF HIGHER FATTY MONOGLYCERIDE MONOSULFATE DETERGENTS

[75] Inventor: Fahim U. Ahmed, Dayton, N.J.

[73] Assignee: Colgate-Palmolive Company, Piscataway, N.J.

[21] Appl. No.: 96,102

[22] Filed: Sep. 14, 1987

[51] Int. Cl.[4] .................. C07C 143/90; C11D 1/28
[52] U.S. Cl. ................................ 260/400; 558/32
[58] Field of Search ........................ 260/400; 558/32

[56] References Cited

U.S. PATENT DOCUMENTS

| | | | |
|---|---|---|---|
| 2,006,309 | 6/1935 | Clark | 260/400 |
| 2,130,361 | 9/1938 | Muncie | 260/400 |
| 2,163,133 | 6/1939 | Schrawth | 538/32 |
| 2,204,433 | 6/1940 | Muncie et al. | 260/400 |
| 2,235,098 | 3/1941 | Brandt et al. | 260/400 |
| 2,242,979 | 5/1941 | Muncie | 260/400 |
| 2,687,420 | 8/1954 | Brady | 260/400 |
| 2,868,812 | 1/1959 | Cray | 260/400 |
| 2,979,521 | 4/1961 | Cray | 260/400 |
| 3,167,570 | 1/1965 | Bohunek | 260/400 |

FOREIGN PATENT DOCUMENTS 666206  2/1952  United Kingdom ............... 260/400

*Primary Examiner*—Patrick P. Garvin
*Assistant Examiner*—E. D. Irzinsiu
*Attorney, Agent, or Firm*—Richard J. Ancel; Robert C. Sullivan; Murray M. Grill

[57] ABSTRACT

A process for the manufacture of water soluble higher fatty monoglyceride monosulfate detergents is described which includes reacting a sulfating agent, such as chlorosulfuric acid, with glycerol dissolved in an organic solvent, such as chloroform, to trisulfate the glycerol, reacting the glycerol trisulfuric acid made with a higher fatty acid or a higher fatty acid methyl ester in such a solvent, extracting the reaction mixture with a solvent for the monoglyceride disulfuric acid, such as aqueous lower alkanol, and neutralizing the extracted monoglyceride disulfuric acid with an aqueous neutralizing agent to make the water soluble detergent salt. Among preferable detergent salts made are sodium hydrogenated coco fatty monoglyceride sulfate, sodium hydrogenated palm kernel fatty monoglyceride sulfate, sodium hydrogenated palm fatty monoglyceride sulfate, sodium hydrogenated tallow fatty monoglyceride sulfate, and mixtures of two or more thereof. In modifications of the processes the extraction and neutralization operations are effected simultaneously, preferably with a slurry of sodium bicarbonate, as neutralizing agent, in aqueous lower alkanol. The products resulting are of improved quality and of higher detergent content and the processes are more efficient, requiring only stoichiometric amounts of reagents, reducing formation of sodium sulfate and improving the yields of detergent, compared to similar prior art products and processes for the production thereof.

6 Claims, No Drawings

PROCESS FOR THE MANUFACTURE OF HIGHER FATTY MONOGLYCERIDE MONOSULFATE DETERGENTS

This invention relates to a process for manufacturing a synthetic organic detergent. More particularly, it relates to a process for making a fatty monoglyceride monosulfate detergent.

Higher fatty monoglyceride monosulfate detergents of the formula

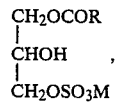

wherein R is a higher fatty alkyl radical of 7 to 17 carbon atoms and M is an alkali metal, ammonium, or triethanolamine, are well known and have been employed as mild and effective anionic detergents in shampoos, unbuilt detergent powders, synthetic detergent bars and combination soap-synthetic detergent bars. Such detergents have been manufactured by reacting fatty materials with large excesses of sulfating agents and neutralizing the sulfated monoglycerides made. Also, monoglycerides have been sulfated and then neutralized to produce the desired monoglyceride sulfates Another process utilizes chloroform as a solvent for a monoester of a polyol (or diol), with chlorosulfuric acid being employed to sulfate the polyol, after which the sulfuric acid compound made is neutralized with ammonia or other neutralizing agent. In another reaction for the production of monoglyceride sulfates a triglyceride is reacted with glycerol trisulfuric acid and a large excess of sulfuric acid, after which the monoglyceride sulfuric acid resulting is neutralized.

While such processes are effective for manufacturing the desired higher fatty monoglyceride monosulfate detergents, often such detergents include substantial proportions of inorganic sulfate byproduct and therefore are low in active ingredient (A.I.) or detergent content. Practicing the process of the present invention allows the utilization of approximately stoichiometric proportions of reactants (instead of large excesses as are sometimes required in other processes), and results in products which are of higher A.I. and lower inorganic sulfate contents, without final alcoholic extractions Among patents found in a search for art which could be relevant to this invention there are included U.S. Pat. Nos. Re. 20,636 (U.S. Pat. No. Re. 2,023,387), 2,212,521 and 2,868,812. However, such patents are not considered to anticipate or make obvious the subject matter of the present application.

In accordance with the present application, a process for the manufacture of a water soluble salt of a higher fatty monoglyceride monosulfuric acid comprises reacting about three molar proportions of a sulfating agent with one molar proportion of glycerol dissolved in an organic solvent at a temperature in the range of 10° C. to 60° C. so that the glycerol is completely sulfated to the trisulfuric acid thereof, reacting the glycerol trisulfuric acid made with a higher fatty acid or higher fatty acid methyl ester in such a solvent for thirty minutes to five hours, extracting the reaction mixture with an aqueous organic solvent for the monoglyceride disulfuric acid produced and neutralizing and hydrolyzing the monoglyceride disulfuric acid with aqueous neutralizing agent to make a water soluble salt of monoglyceride monosulfuric acid.

The following equations illustrate the reactions of the present invention.

Stage 1:
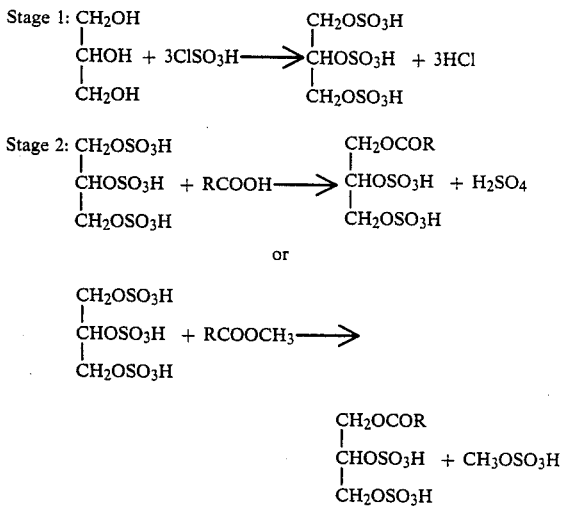

Extraction of Stage 2 Product:
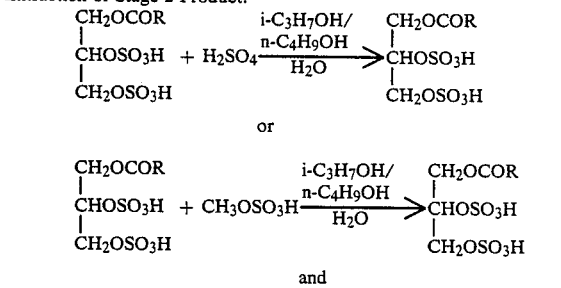

Stage 3:
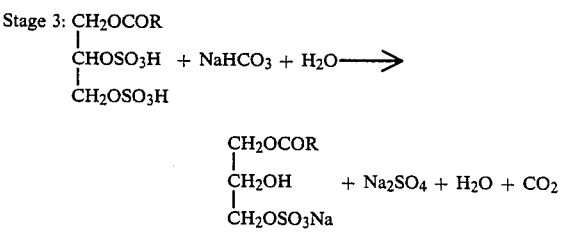

In the Stage 1 reaction gylcerol is slowly sulfated with chlorosulfuric acid in chloroform, preferably at about ambient temperature. Hydrochloric acid gas, which is generated by the reaction, may be vented and diluted in cold water. However, it can be scrubbed and may be reacted with sulfur trioxide gas to produce more chlorosulfuric acid. Alternatively, a gaseous mixture of sulfur trioxide in air can be used to partially sulfate the glycerol at a temperature in the range of 35° to 65° C. to produce a product of about 2 degrees of sulfation, which product may be further sulfated to 3 degrees of sulfation by oleum or other strong form of sulfuric acid.

In the Stage 2 reaction the fatty acid and/or methyl ester is/are dissolved in additional chloroform and added to the glycerol trisulfuric acid, and the condensation reaction occurs, with digestion. The employment of chloroform or other suitable solvent in Stages 1 and 2 reduces the viscosity of the reaction medium and facilitates smooth agitation and mixing of the various reagents The chloroform may be recovered from the Stage 2 products by vaporization and condensation during the digestion period or thereafter, or it may be left in the reaction mixture. The extraction, neutralization, and hydrolysis of the detergent diacid are then carried out. The detergent acid may be extracted with a mixture of lower alcohol and water, preferably isopropanol and/or n-butanol and water, and then may be neutralized and hydrolyzed, preferably with a 20 to 35% aqueous sodium hydroxide solution (e.g., about 30% by weight), or neutralization, hydrolysis and extraction may be carried out simultaneously, employing sodium bicarbonate as the dispersed phase in an aqueous n-butanol/isopropanol medium. Of the two methods it is preferred to utilize the combined neutralization and extraction. Thus, when the "brown acid" mixture of Stage 2 is slowly added to a slurry of sodium bicarbonate in isopropanol or n-butanol, or in mixed isopropanol and n-butanol, with vigorous stirring and maintaining of the pH of the mixture near neutrality (in the range of 6 to 7), the brown color of the acid slowly disappears. The final pH of the mixture, after addition of all the bicarbonate slurry, is adjusted to 6.5 and the neutralized slurry is heated for about 30 minutes to a temperature of 40° to 60° C., and filtered to remove the insoluble inorganic salt (sodium sulfate). Following such filtration the solvent is removed by use of a rotary evaporator and the product is vacuum dried to produce the dried monoglyceride monosulfate as the sodium salt.

The described synthesis has been illustrated with respect to any higher fatty acid or its methyl ester, or mixtures thereof but it is considered most desirable to employ saturated fatty acids or their methyl esters to avoid any complicating side reactions of olefinic linkages with sulfating agents. For such reasons, when employing mixed fatty acids or their methyl esters that are obtained from natural oils or fats it will be preferred if such are hydrogenated, such as hydrogenated coconut oil, hydrogenated palm kernel oil, hydrogenated palm oil or hydrogenated tallow, or mixtures thereof.

The higher fatty acid or higher fatty acid lower alkyl ester employed in the invented processes will be one wherein the higher fatty acyl is of 8 to 18 carbon atoms (and the lower alkyl is of 1 to 3 carbon atoms, preferably methyl). Such higher fatty acyl moiety is alkanoyl or alkenoyl (of an alkanoic or alkenoic acid) or a mixture thereof. Such acids include lauric, myristic, palmitic, oleic and stearic acids, to name a few, and naturally occurring mixtures thereof which are obtainable from various vegetable and animal oils and fats, including coconut oil, palm kernel oil, palm oil, tallow and such oils and fats which have been hydrogenated (to decrease or eliminate unsaturation).

The glycerol employed may be synthetic or that which is derived from the splitting of fats and oils, such as occurs in soapmaking. The inventive process is applicable to the production of analogous higher fatty acyl polyol sulfates, such as those of sugars and starches, and polyoxyethylene polyols. However, the invention is considered to be most desirably employed in the manufacturing of monoglyceride monosulfate detergents and, accordingly, this specification and the claims are directed primarily to such processes.

The sulfating agent employed is most preferably chlorosulfuric acid ($ClSO_3H$) but other sulfating agents may also be utilized, such as gaseous or liquid sulfur trioxide, oleum, sulfuric acid, fuming sulfuric acid, and mixtures thereof.

The solvents and media for reaction that are employed are preferably organic solvents of a limited polarity, which is preferably like that of chloroform. In fact, chloroform is the preferred solvent but others, such as hexane and other suitable hydrocarbons, halogenated hydrocarbons, including carbon tetrachloride, trichloroethylene, ethylene dichloride, carbon disulfide, and the various fluorinated hydrocarbons and chlorofluorinated hydrocarbons known as Freons ®, may also be employed. It is often desirable that such solvents be comparatively low boiling so that they may be easily evaporated from the reaction mixture after completion of digestion and before neutralization of the detergent acid The extracting medium or solvent utilized, which helps to separate the monoglyceride disulfuric acid made in the sulfation reaction from sulfuric acid or the monomethyl ester of sulfuric acid (which results from reactions utilizing methyl ester of higher fatty acid in the condensation-digestion step), is preferably an aqueous alcoholic medium in which the alcohol is a lower alkanol of 1 to 4 carbon atoms, preferably isopropyl alcohol or normal butyl alcohol or a mixture thereof.

The neutralizing agent is an aqueous solution of an alkali metal hydroxide, an alkali metal carbonate, an alkali metal bicarbonate, ammonium hydroxide, ammonium carbonate, ammonium bicarbonate, triethanolamine or a mixture or plurality thereof, with sodium hydroxide being the preferred neutralizing agent, and sodium carbonate and sodium bicarbonate also being very useful to make the sodium monoglyceride monosulfate detergents according to the processes of this invention.

In some instances the extraction and neutralization/hydrolysis operations may be conducted simultaneously, in which cases it is preferable to employ a slurry of sodium bicarbonate neutralizing agent in an aqueous lower alcoholic medium. After manufacture of the detergent salt by the method described and with the reagents mentioned, a further extraction may be effected, wherein any inorganic salt, such as sodium sulfate, which might remain with the desired detergent salt, may be separated from it by further extraction with a lower alcohol or an aqueous solution of such lower alcohol of 1 to 3 or 4 carbon atoms, but such extra extraction is not need.

The proportions of sulfating agent and glycerol will be equivalent proportions, which normally will include three molar proportions of sulfating agent and one molar proportion of glycerol. It may sometimes be desirable to utilize a small excess of sulfating agent, such as up to 3.2 moles thereof per mole of glycerol. If the sulfating agent is to be sulfur trioxide, trisulfation of the glycerol may not be obtainable and so a greater excess of sulfur trioxide may be employed and a second stage of sulfation may be desirable, such as that effected by a stronger sulfating agent, e.g., oleum. However, when chlorosulfuric acid is employed stoichiometric proportions may be utilized (3:1).

The glycerol employed will be dissolved in chloroform or other suitable solvent, (with the weight of chloroform being from equal to three times that of glycerol, preferably about twice the weight of glycerol). The reaction temperature will most preferably be held to less than 30° C. However, such temperature range may be 10° to 60° C., preferably 15° or 20° to 50° or 40° C., and in some instances may be as low as 0° C., and the reaction will still proceed satisfactorily. After the completion of the sulfation reaction, which normally will take from 30 minutes to five hours, the glycerol trisulfuric acid is condensed with higher fatty acid or monomethyl ester of such higher fatty acid. Such condensation reaction, which may sometimes be referred to as a digestion step, is carried out using equimolar proportions of glycerol trisulfuric acid and fatty acid or fatty acid methyl (or other lower alkyl) ester. Variations from such equimolar proportions may be ±5 or ±10% under particular circumstances, but it is preferred that equimolar proportions be used. During the condensation or digestion reaction additional chloroform or other solvent may be employed, with the total weight of such solvent normally being up to four times the total of the weights of glycerol trisulfuric acid and higher fatty acid or higher fatty acid lower alkyl ester. The temperature of the reaction should be in the range of 20° to 80° C., preferably 30° to 60° C. and more preferably 40° to 55° C.

In the extraction step, which follows next, a suitable aqueous-organic solvent is employed, normally with from one part of water to two to four parts of solvent. The solvent is desirably a lower alkanol of one to four carbon atoms per mole, preferably n-butanol or isopropanol or a mixture thereof, such as one of weight ratio in the range of 1:4 to 4:1. The temperature of the extraction is desirably held in the 10° to 60° C. range, preferably 30° to 50° C.

Subsequent to extraction, which removes the monoglyceride disulfuric acid from the sulfuric acid or monomethyl ester of sulfuric acid, the monoglyceride disulfuric acid is hydrolyzed and neutralized with sodium hydroxide or other suitable neutralizing agent to produce the desired salt. In the neutralization reaction the water present hydrolyzes the sulfuric acid moiety joined to the central carbon of the glyceryl nucleus, converting it to hydroxyl, while also converting the monoglyceride disulfuric acid to sodium monoglyceride monosulfate salt. The byproduct sodium sulfate may be removed by alcoholic extraction and any water or alcohol still present with the desired detergent salt may be evaporated, or may be left with the detergent salt as solvent(s) for it, if desired.

Alternative to the sequential extraction and neutralization steps is a combined extraction-neutralization operation. In such an operation the preferred neutralizing agent will be sodium bicarbonate or sodium carbonate in an aqueous or alcoholic medium. In the neutralization reactions it is desirable to employ a stoichiometric proportion of the neutralizing agent, but sometimes slight excesses, such as 10%, may be used. The amount of water present in the portion of the combined extraction and neutralizing agent will be at least a hydrolyzing proportion and the alcohol content will be $\frac{1}{4}$ to 4 times the water content. The combined extraction and neutralizing/hydrolyzing medium will normally be maintained at a temperature in the range of 10° to 60° C. and will be stirred continuously and preferably vigorously during the extraction-neutralization operation, with the pH thereof being maintained in the range of 6.0 to 7.0 and normally being about 6.5 at the conclusion of the neutralization reaction, at which point the desired monoglyceride monosulfate detergent will have been produced. The insoluble inorganic salt, such as sodium sulfate byproduct, may be removed from the detergent by filtration. Any lower alcohol and any chloroform remaining may be removed from the detergent by vaporization. If further purification of the detergent salt is desired, it may be carried out by further alcoholic extraction and filtration of the insoluble salt, but it is an advantage of the invention that such additional extraction-filtration operation is not necessary.

The following examples illustrate the invention but do not limit it. Unless otherwise indicated, all parts and percentages in the examples, specification and claims are by weight and all temperatures are in °C.

EXAMPLE 1

(Synthesis of Sodium Hyrogenated Coco Monoglyceride Monosulfate)

Chlorosulfuric acid (93.2 g., 0.8 mole) is dissolved in 100 ml. of chloroform and such solution is added dropwise to glycerol (23.0 g., 0.25 mole), which is in a one liter three-necked flask equipped with a mechanical stirrer, a dropping funnel, a thermometer and a pressure outlet, connected to an oil bubbler. The flask is maintained externally cooled by an ice bath so the reaction temperature during the period when the chlorosulfuric acid is added to glycerine can be maintained below 30° C. The chlorosulfuric acid is added dropwise to the glycerol with vigorous stirring over a period of about 0.5 hour, after which the stirring of the reaction mixture is continued, at room temperature, without addition of more chlorosulfuric acid, for about another half hour to expel all gaseous hydrogen chloride. The reaction mix is viscous and slightly brownish in color.

To the glycerol trisulfuric acid made by the previously described reaction, there is added hydrogenated coconut oil fatty acid (51.4 g., 0.25 mole), in solution in 100 ml. of chloroform. The addition is slow and the temperature of the reaction mixture gradually increases to about 40° C. The reaction mixture is then heated and maintained at about 65° C. by a hot water bath for about 1.5 hours, and about 170 ml. of chloroform are recovered by vaporization and condensation.

The viscous reaction mix resulting is cooled by an ice bath to 10° C. and a mixture of 700 g. of ice and 700 ml. of n-butanol is slowly introduced into the reaction flask with stirring. The liquid mixture resulting is stirred for an additional half hour, while being kept cool on an ice bath. The upper alcoholic layer separates and in it there is contained the monoglyceride disulfuric acid resulting from reaction of the higher fatty acid and glycerol trisulfuric acid. The aqueous lower layer is extracted with two 100 ml. portions of n-butanol and the combined alcohol extracts are washed with 200 ml. of water. The washed alcohol extract is cooled on an ice bath and is slowly neutralized (and hydrolyzed) with aqueous sodium hydroxide (30% concentration) to a pH of 6.5.

The solvent is removed from the neutralized and hydrolyzed mixture by a rotary evaporator. The remaining material is stirred with 500 ml. of acetone and is filtered (the sodium coco monoglyceride monosulfate is insoluble in acetone), after which any solvent present is removed by subjection of the filtered out material to vacuum (vacuum pumping).

The product obtained is analyzed by cationic titration with benzethonium chloride, using methylene blue as the indicator, and is found to be 93% active detergent salt. The yield of product is 82.4 g., which corresponds to a yield of 85%, based on the product, or 79%, based on the active detergent content thereof.

EXAMPLE 2

(Synthesis of Sodium Hydrogenated Palm Kernel Monoglyceride Monosulfate)

Chlorosulfuric acid (93.2 g., 0.8 mole) is dissolved in 50 ml. of chloroform and such solution is added dropwise to a cold (10° C.) dispersion of glycerol (23.0 g., 0.25 mole) in 50 ml. of chloroform over a period of 0.5 hour. The hydrogen chloride evolved is vented. The semi-solid material produced is stirred at ambient temperature for about 0.5 hr. to expel the remaining gaseous hydrogen chloride.

Hydrogenated palm kernel oil fatty acid methyl ester (57.7 g., 0.25 mole) is dissolved in 100 ml, of chloroform and is slowly added to the glycerol trisulfuric acid previously made. The solution resulting is heated to a temperature of 63°-65° C. for two hours, and chloroform is vaporized off and recovered. The viscous material resulting is cooled on an ice bath and 600 ml.of n-butanol and 700 g. of ice are slowly added to it. Such mixture is stirred for 0.5 hr. and an upper alcohol layer that is formed is separated from a lower aqueous layer. The lower layer is extracted with two 150 ml. portions of n-butanol. The alcohol extracts are combined and the combined extract is washed with 300 ml. of water.

The washed alcohol solution of monoglyceride disulfuric acid is then neutralized with aqueous sodium hydroxide solution to a pH of 6.5. The solvent is removed by rotary evaporation and 123.2 g. of material remain. This material is stirred with 600 ml. of acetone, filtered and vacuum dried, yielding 83 g. of solid product, which analyzes to be 67.6% of active detergent salt. Thus, the yield is 57%.

EXAMPLE 3

(Synthesis of Sodium Hyrogenated Palm Monoglyceride Monosulfate)

Chlorosulfuric acid (384.5 g., 3.3 moles) is dissolved in 100 ml. of chloroform. Glycerol (92.1 g., 1 mole) is added slowly, over a period of 0.5 hr., to the stirred solution of chlorosulfuric acid in chloroform, which is in a two liter, three-necked, round bottom flask, while maintaining the reaction mixture at a temperature of less than 30° C. by means of an ice bath. Hydrogen chloride is evolved during the reaction and is vented through a bubbler into ice cold water. Subsequently, the viscous product resulting (glycerol trisulfuric acid) is stirred for an additional 0.5 hour to remove any remaining hydrogen chloride.

Hyrogenated palm oil acid (273.6 g., 1 mole) is partially dissolved in 300 ml. of chloroform and the solution-dispersion resulting is slowly added to the glycerol trisulfuric acid previously made. An additional 50 ml. of chloroform are added and the reaction mixture is heated and refluxed for two hours, after which it is cooled and transferred to a separatory funnel. The desired reaction product in the separatory funnel is hydrogenated palm monoglyceride disulfuric acid.

A slurry of 460 g. of sodium bicarbonate, 1500 ml. of isopropanol and 600 ml. of water is made and is kept cold, at 10° C., on an ice bath. A pH electrode, which is connected to a pH meter, is inserted into the bicarbonate slurry so that the pH may be monitored during neutralization. The hydrogenated palm monoglyceride disulfuric acid is slowly introduced into the aqueous alcoholic sodium bicarbonate slurry in such manner that the pH is maintained about neutral, in the range of 6.5 to 7.5, although in some instances the range of 6.0 to 7.0 or 7.5 may be used. At the completion of the neutralization of the monoglyderide disulfuric acid the product becomes thick, so 500 ml. of n-butanol are added. The mixture is heated to 60° C., to dissolve all the organic material, and another 500 ml. of isopropanol are added. The mix is then treated with charcoal to improve its color and is cooled to room temperature, at which some detergent salt precipitates, which is filtered out. The filtrate is then cooled to ambient temperature and is concentrated to a solid, after it is combined with the filtered out product. The combined solids are then stirred in 1500 ml. of acetone, using a mechanical stirrer, and are filtered. A solid white material is thus obtained and is vacuum pumped overnight, powdered, and again subjected to vacuum overnight. The total yield of solid is 386 g., and the active detergent content thereof is found by analysis to be 85.3%. The yield is 76.6%.

EXAMPLE 4

(Synthesis of Various Monoglyceride Monosulfates)

Following the procedure of Example 1, sodium (unhydrogenated) coco monoglyceride monosulfate is made, with the sole change in the process being in the employment of a slightly different weight of coco fatty acids due to the slight change in molecular weight (although the molar proportion is the same). The product made is sodium coco monoglyceride monosulfate and the purity and yield are essentially the same as those for the product of Example 1. Similarly, sodium unhydrogenated palm kernel monoglyceride monosulfate and sodium unhydrogenated palm monoglyceride monosulfate are made, using the same weights of the reactants, except for the fatty acids, wherein the same molar proportions are employed. In the same manner the hydrogenated and non-hydrogenated monoglyceride monosulfates of animal fats, such as tallow, are made and in some instances blends of tallow with the various mentioned vegetable oils, and others, are employed instead.

The procedure of Example 2 is followed, utilizing the fatty acid methyl esters of coconut oil, hydrogenated coconut oil, palm kernel oil, palm oil, hydrogenated palm oil, tallow and hydrogenated tallow, and the results are similar. Of course, the reagent weights will differ but the moles are equal.

The process of Example 3, in which a combined neutralization, extraction and hydrolysis is effected, is carried out with the various mentioned fatty acids, hydrogenated fatty acids, fatty acid lower alkyl (methyl) esters and hydrogenated fatty acid lower alkyl (methyl) esters, and the corresponding products are obtained in good yields and purities.

Of course, in the modifications of the basic three examples given above it is sometimes desirable to employ more or less solvent or somewhat different proportions of the reagents to obtain maximum yields and greater purities, but it is considered that such modifications of the invented processes are within the abilities of those skilled in the art who have the present teachings before them.

The invention has been described with respect to various illustrations and embodiments thereof but is not to be limited to these because it will be evident that one of skill in the art, with the present specification before him, will be able to utilize various substitutes and equivalents without departing from the invention.

What is claimed is:

1. A process for the manufacture of sodium higher fatty monoglyceride monosulfate, in which the higher fatty moiety is cocoyl or palm kerneloyl, which comprises reacting about three molar proportions of chlorosulfuric acid with one molar proportion of glycerol, dissolved in chloroform, at a temperature in the range of 10° to 60° C., so that the glycerol is completely sulfated to glycerol trisulfuric acid, reacting the glycerol trisulfuric acid, dissolved in chloroform, with coco or palm kernel fatty acid, or coco or palm kernel fatty acid methyl ester for 30 minutes to five hours at a temperature in the range of 30° to 60° C., extracting the reaction mixture resulting with an aqueous n-butanol solvent at a temperature in the range of 10° to 60° C., to extract the coco or palm kernel monoglyceride disulfuric acid made and neutralizing and hydrolyzing such monoglyceride disulfuric acid extract with a neutralizing agent which is aqueous sodium hydroxide, sodium carbonate or sodium bicarbonate, or a plurality thereof, to produce sodium cocoyl or palm kerneloyl monoglyceride sulfate, and removing water, n-butanol and chloroform from such sodium cocoyl or palm kerneloyl monoglyceride monosulfate by evaportion, to produce sodium cocoyl or palm kerneloyl monoglyceride monosulfate in improved yield.

2. A process according to claim 1 wherein the higher fatty moiety of the fatty monoglyceride monosulfuric acid is hydrogenated cocoyl, the glycerol is dissolved in about twice its weigh of chloroform..rm, the temperature of the chloroform is maintained in the range of 30° to 50° C. during the sulfation of the glycerol, the reaction of the glycerol trisulfuric acid is with hydrogenated coco fatty acid, the extraction of the reaction mixture is with an n-butanol-water mixture in which the weight of water is about equal to that of n-butanol, and the neutralization and hydrolysis of the monoglyceride disulfuric acid is with an aqueous solution of sodium hydroxide.

3. A process according to claim 1 wherein the higher fatty moiety of the fatty monoglyceride monosulfuric acid is hydrogenated palm kerneloyl, the glycerol is dissolved in about twice its weight of chloroform, the temperature of the chloroform is maintained in the range of 30° to 50° C. during the sulfation of the glycerol, the reaction of the glycerol trisulfuric acid is with hydrogenated palm kerneloyl fatty acid, the extraction of the reaction mixture is with an n-butanol-water mixture in which the weight of water is about equal to that of n-butanol, and the neutralization and hydrolysis of the monoglyceride disulfuric acid is with an aqueous solution of sodium hydroxide.

4. A process according to claim 1 wherein the extraction, neutralization and hydrolysis are carried out simultaneously, utilizing a slurry of sodium bicarbonate, as neutralizing agent, in an aqueous lower alcohol medium, which is stirred vigorously while the pH thereof is maintained in the range of 6.0 to 7.0, insoluble inorganic salt is removed, after such extraction, neutralization and hydrolysis, by filtration, and water, lower alkanol and the organic solvent are removed by evaporation, resulting in the production of sodium higher monoglyceride monosulfate in improved yield and of active detergent content over 60%.

5. A process according to claim 1 wherein the higher fatty moiety of the fatty monoglyceride monosulfuric acid is hydrogenated cocoyl, the glycerol is dissolved in twice its weight of chloroform, the temperature of the chloroform is maintained in the range of 20° to 40° C. during the sulfation of the glycerol, the reaction of the glycerol trisulfuric acid made is with hydrogenated coco fatty acid, the extraction, neutralization and hydrolysis are carried out simultaneously, utilizing a slurry of sodium bicarbonate, as neutralizing agent, in the aqueous lower alcoholic medium, which is stirred vigorously while the pH thereof is maintained in the range of 6.0 to 7.0, insoluble inorganic salt is removed by filtration after extraction, neutralization and hydrolysis, and water, lower alkanol and chloroform are removed by evaporation, resulting in the production of sodium hydrogenated cocoyl monoglyceride monosulfate in high yield and of an active ingredient content over 90%.

6. A process according to claim 3 wherein the higher fatty moiety of the fatty monoglyceride monosulfuric acid is hydrogenated palm kerneloyl, the glycerol is dissolved in twice its weight of chloroform, the temperature of the chloroform is maintained in the range of 20° to 40° C. during the sulfation of the glycerol, the reaction of the glycerol trisulfuric acid made is with hydrogenated palm kernel fatty acid, the extraction, neutralization and hydrolysis are carried out simultaneously, utilizing a slurry of sodium bicarbonate, as neutralizing agent, in the aqueous lower alcoholic medium, which is stirred vigorously while the pH thereof is maintained in the range of 6.0 to 7.0, insoluble inorganic salt is removed by filtration after extraction, neutralization and hydrolysis, and water, lower alkanol and chloroform are removed by evaporation, resulting in the production of sodium hydrogenated palm kerneloyl monoglyceride monosulfate in improved yield and of an active detergent content over 65%.

* * * * *